US005965560A

United States Patent [19]
Glase et al.

[11] Patent Number: 5,965,560
[45] Date of Patent: Oct. 12, 1999

[54] SUBSTITUTED PIPERAZINES AND PIPERIDINES AS CENTRAL NERVOUS SYSTEM AGENTS

[75] Inventors: Shelly A. Glase; Terri S. Purchase; Lawrence D. Wise, all of Ann Arbor, Mich.

[73] Assignee: Warner-Lambert Company, Morris Plains, N.J.

[21] Appl. No.: 08/981,442

[22] PCT Filed: Apr. 8, 1997

[86] PCT No.: PCT/US97/05777

§ 371 Date: Dec. 19, 1997

§ 102(e) Date: Dec. 19, 1997

[87] PCT Pub. No.: WO97/41108

PCT Pub. Date: Nov. 6, 1997

Related U.S. Application Data

[60] Provisional application No. 60/016,513, Apr. 30, 1996.

[51] Int. Cl.$^6$ ...................... A61K 31/495; A61K 31/445; C07D 295/096; C07D 401/04
[52] U.S. Cl. .......................... 514/252; 514/254; 514/255; 514/318; 514/320; 514/323; 514/324; 544/360; 544/363; 544/373; 544/376; 544/394; 546/194; 546/196; 546/200; 546/201; 546/202
[58] Field of Search .................................. 544/360, 394, 544/363, 373, 376; 514/252, 254, 255

[56] References Cited

U.S. PATENT DOCUMENTS 4,370,329  1/1983  Scherm et al. ........................... 544/394
4,370,330  1/1983  Scherm et al. ........................... 544/394
4,673,675  6/1987  Robba et al. ............................ 514/252

FOREIGN PATENT DOCUMENTS 007067  1/1980  European Pat. Off. .
177392  4/1986  European Pat. Off. .
385351  9/1990  European Pat. Off. .
390654  10/1990  European Pat. Off. .
624584  11/1994  European Pat. Off. .
2057441  4/1981  United Kingdom .
9622977  8/1996  WIPO .

OTHER PUBLICATIONS

Gazi et al., British Journal of Pharmacology, 124, pp. 889–896, 1998.
TenBrink etr al.,Journal of Medicinal Chemistry, vol. 39, pp. 2435–2437, 1996.
Petrigara et al, *J. Med. Chem. 11*, pp. 332–336 (1968).
Prasad et al, *J. Med. Chem.* 11, pp. 1144–1150 (1968).
Gootjes et al, *Arzneimittel–Forschung* 17(9), pp. 1145–1149 (1967).
Reynolds, *Drugs,* 51, pp. 7–11 (1996).
Rulagowski et al, *Current Pharmaceutical Design 3*, pp. 355–366 (1997).

*Primary Examiner*—Emily Bernhardt
*Attorney, Agent, or Firm*—Francis J. Tinney

[57] ABSTRACT

Substituted piperazines and piperidines and derivatives thereof are described, as well as methods for the preparation and pharmaceutical composition of same, which are useful as central nervous system agents and are particularly useful as dopamine antagonists and antipsychotic agents.

6 Claims, No Drawings

SUBSTITUTED PIPERAZINES AND PIPERIDINES AS CENTRAL NERVOUS SYSTEM AGENTS

This application is a 371 of PCT/US97/05777 filed Apr. 8, 1997, which claims the benefit of U.S. Provisional Application No. 60/016,513 filed Apr. 30, 1996.

BACKGROUND OF THE INVENTION

The present invention relates to novel substituted piperazines and piperidines and derivatives thereof useful as pharmaceutical agents, to methods for their production, to pharmaceutical compositions which include these compounds and a pharmaceutically acceptable carrier, and to pharmaceutical methods of treatment. The novel compounds of the present invention are central nervous system agents. More particularly, the novel compounds of the present invention are dopamine antagonists.

Dopamine (DA) D2 antagonists are established as antipsychotic agents. Undesired consequences of DA D2 antagonism are extrapyramidal side effects and tardive dyskinesia. More recently, the DA D4 receptor has been identified as having a possible role in schizophrenia. The atypical antipsychotic drug clozapine has a tenfold higher affinity for the DA D4 receptor than the D2 (Van Tol H. H. J., Bunzow J. R., Guan H. -C., et al., "Cloning of a human dopamine D4 receptor gene with high affinity for the antipsychotic clozapine." *Nature*, 1991;350:614–619) and is notable for its lack of extrapyramidal side effects and tardive dyskinesia. The levels of mRNA for the D4 receptor are much higher in the frontal cortex and limbic region, which are associated with cognitive and emotional function, than in the striatum, which is associated with movement (Van Tol, et al., supra, 1991). In addition, Seeman P., Guan H. -C., and Van Tol H. H. M., "Dopamine D4 receptors elevated in schizophrenia," *Nature*, 1993;365:441–445 has reported a sixfold increase of the D4 recept or number in postmortem specimens from patients with schizophrenia compared to controls.

The compounds of the present invention were shown to selectively bind to the DA D4 receptor while having weak affinity for the DA D2 and DA D3 receptors.

A series of piperazines represented by the Formula I

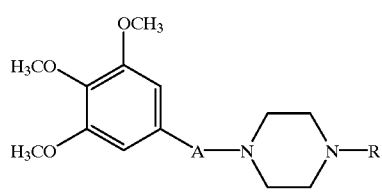

A=CO, COCH$_2$, COCH$_2$CH$_2$, CH(OH)CH$_2$CH$_2$, COCH$_2$CH$_2$CH$_2$, or CH(OH)CH$_2$CH$_2$CH$_2$
R=CH$_3$, 2-(2'-hydroxyethoxy)ethyl, cyclohexyl, benzyl, m-methyl-, or p-t-butylbenzyl, phenethyl, C$_6$H$_5$, o- or p-chlorophenyl, o-, m-, or p-methoxyphenyl, o-, m-, or p-tolyl, 2,6-xylyl, 2-pyridyl, 2-pyrimidyl, or 2-thiazolyl are disclosed by Petigara R. B., et al., *Journal of Medicinal Chemistry*, 1968;11:332–336 as central nervous system depressants.

A series of arylpiperazines represented by the Formula I

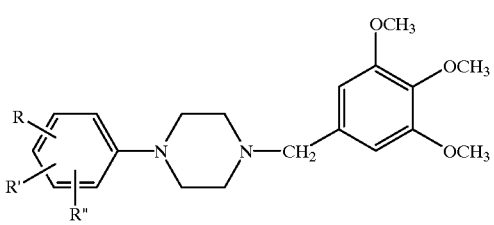

wherein R is hydrogen, trifluoromethyl, hydroxy, nitro, halogen, lower alkyl, or lower alkoxy;

R' is hydrogen, trifluoromethyl, halogen, lower alkyl, or lower alkoxy; and

R" is hydrogen or lower alkoxy; or two of R, R', and R" are lower alkylenedioxy; or an acid addition salt thereof are disclosed in United Kingdom Published Patent Application GB 2,057,441A as having circulation-enhancing activity.

The compounds of the present invention, unlike the compounds disclosed in Petigara R. B., et al., supra, (1968) and United Kingdom Published Patent Application GB 2,057,441A, interact selectively with the DA D4 receptor. Thus, the compounds of the present invention are DA D4 selective antagonists which are useful in the treatment of psychosis such as schizophrenia without the extrapyramidal side effects associated with an agent that interacts with the DA D2 receptor.

SUMMARY OF THE INVENTION

Accordingly, a first aspect of the present invention is a compound of Formula I

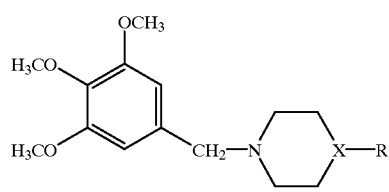

wherein X is N or CH; and

R is aryl or heteroaryl; or a pharmaceutically acceptable acid additional salt thereof;

with the proviso that when X is N and R is aryl, aryl is not phenyl, phenyl monosubstituted by lower alkyl, lower alkoxy, halogen, or nitro, phenyl disubstituted by lower alkyl, or phenyl trisubstituted by lower alkoxy.

A second aspect of the present invention is a compound of Formula Ia

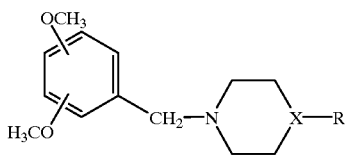

wherein X is N or CH; and
R is aryl or heteroaryl; or a pharmaceutically acceptable acid addition salt thereof; with the following provisos:

(a) that when X is N or CH, and R is aryl, aryl is not phenyl, or
  phenyl monosubstituted by
    lower alkyl,
    lower alkoxy, or
    halogen; and
(b) that when X is N and R is heteroaryl, heteroaryl is not 2-, 3-, or 4-pyridinyl.

As dopamine antagonists, the compounds of Formula I and Formula Ia are antipsychotic agents useful for treating psychoses such as schizophrenia.

A still further embodiment of the present invention is a pharmaceutical composition for administering an effective amount of a compound of Formula I or Formula Ia in unit dosage form in the treatment methods mentioned above.

Finally, the present invention is directed to a method for production of a compound of Formula I or Formula Ia.

DETAILED DESCRIPTION OF THE INVENTION

In the compounds of Formula I or Formula Ia, the term "lower alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "aryl" means an aromatic radical which is a phenyl group or phenyl group substituted by 1 to 4 substituents selected from lower alkyl, lower alkoxy, lower thioalkoxy, halogen, nitro, amino, or cyano, such as, for example, 2-chlorophenyl, 3-chlorophenyl, 4-chlorophenyl, 2-methylphenyl, 3-methylphenyl, 4-methylphenyl, 2-methoxyphenyl, 3-methoxyphenyl, 4-methoxyphenyl, 2-chloro-3-methylphenyl, 2-chloro-4-methylphenyl, 2-chloro-5-methylphenyl, 3-chloro-2-methylphenyl, 3-chloro-4-methylphenyl, 4-chloro-2-methylphenyl, 4-chloro-3-methylphenyl, 5-chloro-2-methylphenyl, 2,3-dichlorophenyl, 2,5-dichlorophenyl, 3,4-dichlorophenyl, 2,3-dimethylphenyl, 3,4-dimethylphenyl, and the like.

The term "heteroaryl" means a heteroaromatic radical which is 2-, 3- or 4-pyridinyl 4-, 5-, 6-, or 7-benzo[b]furanyl, 4-, 5-, 6-, or 7-benzo[b]thienyl, 4-, 5-, 6-, or 7-indolyl, 2-, 3-, 4-, 5-, 6-, 7-, or 8-quinolinyl, 2-, 3-, 4-, 5-, 6-, 7-, or 8-isoquinolinyl.

"Lower alkoxy" and "lower thioalkoxy" are O-alkyl or S-alkyl of from 1 to 6 carbon atoms as defined above for "lower alkyl."

"Halogen" is fluorine, chlorine, bromine, or iodine.

The term "host" means mammals which includes humans.

Pharmaceutically acceptable acid addition salts of the compounds of Formula I or Formula Ia include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *Journal of Pharmaceutical Science,* 1977;66:1–19).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

A preferred compound of Formula I is one wherein R is phenyl,
  phenyl substituted by 1 to 3 substituents selected from the group consisting of:
    lower alkyl,
    lower alkoxy,
    lower thioalkoxy,
    halogen,
    nitro,
    amino, and
    cyano,
  2-, 3-, or 4-pyridinyl, 4-, 5-, 6-, or 7-benzo[b]furanyl, 4-, 5-, 6-, or 7-benzo[b]thienyl, 4-, 5-, 6-, or 7-indolyl, 2-, 3-, 4-, 5-, 6-, 7-, or 8-quinolinyl, or 2-, 3-, 4-, 5-, 6-, 7-, or 8-isoquinolinyl; with the proviso that when X is N, R is not phenyl,
    phenyl monosubstituted by
      lower alkyl,
      lower alkoxy,
      halogen, or
      nitro,
    phenyl disubstituted by lower alkyl, or phenyl trisubstituted by lower alkoxy.

A more preferred compound of Formula I is one where in R is phenyl,
  phenyl substituted by 1 to 2 substituents selected from the group consisting of:
    lower alkyl,
    lower alkoxy, and
    halogen, or
  2-pyridinyl; with the proviso that when X is N, R is not phenyl, phenyl monosubstituted by
  lower alkyl,
  lower alkoxy, or
  halogen, or
phenyl disubstituted by lower alkyl.

A most preferred compound of Formula I is one wherein R is phenyl,
phenyl substituted by 1 to 2 substituents selected from the group consisting of:
  methyl,
  methoxy, and
  chloro, or
2-pyridinyl; with the proviso that when x is N, R is not phenyl,
  phenyl monosubstituted by
    methyl,
    methoxy, and
    chloro, or
  phenyl disubstituted by methyl.

Particularly valuable compounds of Formula I are:
  1-(2,5-dichlorophenyl)-4-(3,4,5-trimethoxybenzyl)-piperazine;
  1-(2,3-dichlorophenyl)-4-(3,4,5-trimethoxybenzyl)-piperazine;
  1-(3,4-dichlorophenyl)-4-(3,4,5-trimethoxybenzyl)-piperazine;
  1-(2,3-dimethylphenyl)-4-(3,4,5-trimethoxybenzyl)-piperazine;
  1-(3,4-dimethylphenyl)-4-(3,4,5-trimethoxybenzyl)-piperazine;
  1-(2-chloro-3-methylphenyl)-4-(3,4,5-trimethoxybenzyl)piperazine;
  1-(2-chloro-4-methylphenyl)-4-(3,4,5-trimethoxybenzyl)piperazine;
  1-(2-chloro-5-methylphenyl)-4-(3,4,5-trimethoxybenzyl)piperazine;
  1-(3-chloro-2-methylphenyl)-4-(3,4,5-trimethoxybenzyl)piperazine;
  1-(3-chloro-4-methylphenyl)-4-(3,4,5-trimethoxybenzyl)piperazine;
  1-(5-chloro-2-methylphenyl)-4-(3,4,5-trimethoxybenzyl)piperazine;
  1-(4-chloro-2-methylphenyl)-4-(3,4,5-trimethoxybenzyl)piperazine;
  1-(4-chloro-3-methylphenyl)-4-(3,4,5-trimethoxybenzyl)piperazine;
  1-pyridin-2-yl-4-(3,4,5-trimethoxybenzyl)-piperazine; and
  4-phenyl-1-(3,4,5-trimethoxybenzyl)piperidine; or a pharmaceutically acceptable acid addition salt thereof.

Furthermore, particularly valuable compounds of Formula I used in the methods of the present invention are:
  1-phenyl-4-(3,4,5-trimethoxybenzyl)piperazine;
  1-(2-chlorophenyl)-4-(3,4,5-trimethoxybenzyl)-piperazine;
  1-(3-chlorophenyl)-4-(3,4,5-trimethoxybenzyl)-piperazine;
  1-(4-chlorophenyl)-4-(3,4,5-trimethoxybenzyl)-piperazine;
  1-o-tolyl-4-(3,4,5-trimethoxybenzyl)piperazine;
  1-m-tolyl-4-(3,4,5-trimethoxybenzyl)piperazine;
  1-p-tolyl-4-(3,4,5-trimethoxybenzyl)piperazine;
  1-(2-methoxyphenyl)-4-(3,4,5-trimethoxybenzyl)-piperazine;
  1-(3-methoxyphenyl)-4-(3,4,5-trimethoxybenzyl)-piperazine;
  1-(4-methoxyphenyl)-4-(3,4,5-trimethoxybenzyl)-piperazine;
  1-(2,5-dichlorophenyl)-4-(3,4,5-trimethoxybenzyl)-piperazine;
  1-(2,3-dichlorophenyl)-4-(3,4,5-trimethoxybenzyl)-piperazine;
  1-(3,4-dichlorophenyl)-4-(3,4,5-trimethoxybenzyl)-piperazine;
  1-(2,3-dimethylphenyl)-4-(3,4,5-trimethoxybenzyl)-piperazine;
  1-(3,4-dimethylphenyl)-4-(3,4,5-trimethoxybenzyl)-piperazine;
  1-(2-chloro-3-methylphenyl)-4-(3,4,5-trimethoxybenzyl)piperazine;
  1-(2-chloro-4-methylphenyl)-4-(3,4,5-trimethoxybenzyl)piperazine;
  1-(2-chloro-5-methylphenyl)-4-(3,4,5-trimethoxybenzyl)piperazine;
  1-(3-chloro-2-methylphenyl)-4-(3,4,5-trimethoxybenzyl)piperazine;
  1-(3-chloro-4-methylphenyl)-4-(3,4,5-trimethoxybenzyl)piperazine;
  1-(5-chloro-2-methylphenyl)-4-(3,4,5-trimethoxybenzyl)piperazine;
  1-(4-chloro-2-methylphenyl)-4-(3,4,5-trimethoxybenzyl)piperazine;
  1-(4-chloro-3-methylphenyl)-4-(3,4,5-trimethoxybenzyl)piperazine;
  1-pyridin-2-yl-4-(3,4,5-trimethoxybenzyl)-piperazine; and
  4-phenyl-1-(3,4,5-trimethoxybenzyl)piperidine; or a pharmaceutically acceptable acid addition salt thereof.

A preferred compound of Formula Ia is one wherein R is phenyl,
phenyl substituted by 1 to 3 substituents selected from the group consisting of:
  lower alkyl,
  lower alkoxy,
  lower thioalkoxy,
  halogen,
  nitro,
  amino, and
  cyano,
2-, 3-, or 4-pyridinyl, 4-, 5-, 6-, or 7-benzo[b]furanyl, 4-, 5-, 6-, or 7-benzo[b]thienyl, 4-, 5-, 6-, or 7-indolyl, 2-, 3-, 4-, 5-, 6-, 7-, or 8-quinolinyl, or 2-, 3-, 4-, 5-, 6-, 7-, or 8-isoquinolinyl; with the following provisos:
  (a) that when X is N or CH, R is not phenyl, or
  phenyl monosubstituted by
    lower alkyl,
    lower alkoxy, or
    halogen, and
  (b) that when X is N, R is not 2-, 3-, or 4-pyridinyl.

A more preferred compound of Formula Ia is one wherein R is phenyl,
phenyl substituted by 1 to 2 substituents selected from the group consisting of:
  lower alkyl,
  lower alkoxy, and
  halogen, or
2-pyridinyl; with the following provisos:
  (a) that when X is N or CH, R is not phenyl,
  phenyl monosubstituted by
    lower alkyl,
    lower alkoxy, or halogen, and (b) that when X is N, R is not 2-pyridinyl.

A most preferred compound of Formula Ia is one wherein R is phenyl, phenyl substituted by 1 to 2 substituents selected from the group consisting of:
methyl,
methoxy, and
chloro, or
2-pyridinyl; with the following provisos:
(a) that when X is N or CH, R is not phenyl,
phenyl monosubstituted by
methyl,
methoxy, and
chloro, and
(b) that when X is N, R is not 2-pyridinyl.

Particularly valuable compounds of Formula Ia are:
1-(2-chloro-3-methylphenyl)-4-(2,3-dimethoxy-benzyl)piperazine;
1-(2-chloro-3-methylphenyl)-4-(2,4-dimethoxy-benzyl)piperazine;
1-(2-chloro-3-methylphenyl)-4-(2,5-dimethoxy-benzyl)piperazine; and
1-(2-chloro-3-methylphenyl)-4-(3,4-dimethoxy-benzyl)piperazine; or a pharmaceutically acceptable acid addition salt thereof.

Furthermore, particularly valuable compounds of Formula Ia used in the methods of the present invention are:
1-(2-chloro-3-methylphenyl)-4-(2,3-dimethoxy-benzyl)piperazine;
1-(2-chloro-3-methylphenyl)-4-(2,4-dimethoxy-benzyl)piperazine;
1-(2-chloro-3-methylphenyl)-4-(2,5-dimethoxy-benzyl)piperazine; and
1-(2-chloro-3-methylphenyl)-4-(3,4-dimethoxy-benzyl)piperazine; or a pharmaceutically acceptable acid addition salt thereof.

The compounds of Formula I and Formula Ia are valuable dopamine antagonists. The tests employed indicate that compounds of Formula I and Formula Ia possess dopamine antagonist activity.

Compounds were tested for their ability to bind to dopamine receptors as measured by their inhibition of [$^3$H] spiperone binding to the human D2, D3 receptors in a receptor assay described by MacKenzie R. G., VanLeeuwen D., Pugsley T. A., et al., "Characterization of the human dopamine D3 receptor expressed in transfected cell lines." Eur. J. Pharmacol.-Mol. Pharmacol., 1994;266:79–85; for the human D4 dopamine receptor in a receptor assay by Pugsley T. A., Davis M. D., Akunne H. C., et al., "CI-1007, a dopamine partial agonist and potential antipsychotic agent. I. Neurochemical Effects." J. Pharmacol. Exp. Ther., 1995;274:898–911; and for ability to block the action of an agonist in a [$^3$H]thymidine incorporation assay described by Lajiness N. E., Chio C. L., Huff R. M., "D2 dopamine receptor stimulation of mitogenesis in transfected Chinese hamster ovary cells: relationship to dopamine stimulation of tyrosine phosphorylations." J. Pharmacol. Exp. Ther., 1993;267:1573–81. This test determines the agonist/antagonist character of a compound by measuring [$^3$H] thymidine update in Chinese hamster ovary (CHO) pro-5 cells expressing the DA D4 receptor. Agonists, such as quinpirole, promote cell growth and subsequent [$^3$H] thymidine incorporation, while antagonists block the action of agonists. Compounds of the present invention were shown to be antagonists by blocking the action of quinpirole. The above test methods are incorporated herein by reference.

The binding data in the table below shows the dopamine antagonist activity of representative compounds of Formula I and Formula Ia.

Biological Activity of Compounds of Formula I and Formula Ia

| Example | Compound | DA D4 Ki (nM) | DA D3 Ki (nM) | DA D2 Ki (nM) |
|---|---|---|---|---|
| 1 | 1-phenyl-4-(3,4,5-trimethoxy-benzyl)piperazine | 6.2 | 1505 | 1022 |
| 7 | 1-m-tolyl-4-(3,4,5-trimethoxy-benzyl)piperazine, monohydrochloride | 8.6 | 2766 | 1456 |
| 8 | 1-p-tolyl-4-(3,4,5-trimethoxy-benzyl)piperazine, monohydrochloride | 7.5 | 6818 | 1415 |
| 19 | 1-(3-chloro-2-methylphenyl)-4-(3,4,5-trimethoxy-benzyl)piperazine, monohydrochloride | 6.1 | 2118 | 1055 |
| 20 | 1-(3-chloro-4-methylphenyl)-4-(3,4,5-trimethoxy-benzyl)piperazine, monohydrochloride | 4.5 | 2025 | 3290 |
| 21 | 1-(5-chloro-2-methylphenyl)-4-(3,4,5-trimethoxy-benzyl)piperazine, monohydrochloride | 6.5 | 3515 | 1565 |
| 26 | 1-(2-chloro-3-methylphenyl)-4-(2,3-dimethoxy-benzyl)piperazine, monohydrochloride | 12.7 | 2646 | 2895 |
| 27 | 1-(2-chloro-3-methylphenyl)-4-(2,4-dimethoxy-benzyl)piperazine | 4.4 | 409 | 762 |
| 28 | 1-(2-chloro-3-methylphenyl)-4-(2,5-dimethoxy-benzyl)piperazine | 11.3 | 730 | 2084 |
| 29 | 1-(2-chloro-3-methylphenyl)-4-(3,4-dimethoxy-benzyl)piperazine, monohydrochloride | 5.0 | 1207 | 2342 |

A compound of Formula I

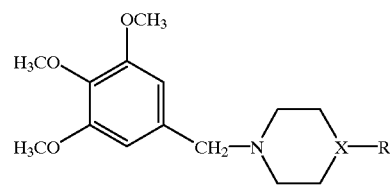

wherein X is N or CH; and

R is aryl or heteroaryl; or a pharmaceutically acceptable acid addition salt thereof may be prepared by reacting a compound of Formula II

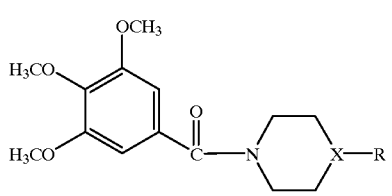

wherein X and R are as defined above in the presence of a metal hydride such as, for example, aluminum hydride and the like in a solvent such as, for example, tetrahydrofuran and the like at about −10° C. to about room temperature for about 10 minutes to about 24 hours to afford a compound of Formula I. Preferably, the reaction is carried out in the presence of aluminum hydride in tetrahydrofuran at about 0° C. for about 2 hours.

A compound of Formula II is prepared from a compound of Formula III

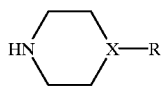

III wherein X and R are as defined above and 3,4,5-trimethoxybenzoyl chloride in the presence of a base such as, for example, triethylamine and the like and a solvent such as, for example, dichloromethane and the like at about room temperature for about 1 hour to about 24 hours to afford a compound of Formula II. Preferably, the reaction is carried out in the presence of triethylamine in dichloromethane at about room temperature for about 2 hours.

A compound of Formula Ia

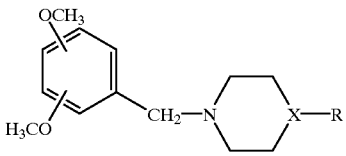

Ia wherein X is N or CH; and

R is aryl or heteroaryl; or a pharmaceutically acceptable acid addition salt thereof may be prepared by reacting a compound of Formula IIa

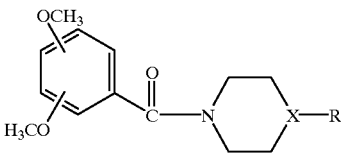

IIa wherein X and R are as defined above using the methodology described for preparing a compound of Formula I from a compound of Formula II to afford a compound of Formula Ia.

A compound of Formula IIa is prepared from a compound of Formula III and a compound of Formula IV

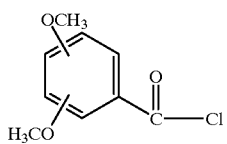

IV using the methodology described for preparing a compound of Formula II from a compound of Formula III and 3,4,5-trimethoxybenzoyl chloride to afford a compound of Formula IIa.

Compounds of Formula III and Formula IV are either known or capable of being prepared by methods known in the art.

The compounds of the present invention can be prepared and administered in a wide variety of oral and parenteral dosage forms. It will be obvious to those skilled in the art that the following dosage forms may comprise as the active component, either a compound of Formula I or Formula Ia or a corresponding pharmaceutically acceptable salt of a compound of Formula I or Formula Ia.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg preferably 10 mg to 100 mg according to the particular application and the potency of the active component. The composition can, if desired, also contain other compatible therapeutic agents.

In therapeutic use as antipsychotic agents, the compounds utilized in the pharmaceutical method of this invention are administered at the initial dosage of about 1 mg to about 50 mg per kilogram daily. A daily dose range of about 5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors preferred methods for preparing the compounds of the invention.

EXAMPLE 1

1-(2-Chloro-3-methylphenyl)-4-(3,4.5-trimethoxybenzyl)-piperazine

Step A: Preparation of [4-(2-chloro-3-methylphenyl)-piperazine-1-yl]-(3,4,5-trimethoxyphenyl)methanone 3,4,5-Trimethoxybenzoyl chloride (2.03 g, 8.8 mmol) in dichloromethane (10 mL) is added dropwise to a solution of 2-chloro-3-methylphenyl piperazine (1.98 g, 8.0 mmol) and triethylamine (4.5 mL, 32.0 mmol) in dichloromethane (90 mL) and stirred for 2 hours at room temperature. The reaction mixture is washed with water, dried (magnesium sulfate), and concentrated in vacuo. The resulting solid is purified by medium pressure liquid chromatography (MPLC) on silica gel eluting with 40% ethyl acetate/hexane to give 2.52 g of the title compound as a white solid; mp 156–159° C.

Step B: Preparation of 1-(2-chloro-3-methylphenyl)-4-(3,4,5-trimethoxybenzyl)piperazine A solution of aluminum chloride (0.279 g, 2.09 mmol) in anhydrous diethyl ether (20 mL) is added dropwise to a suspension of lithium aluminum hydride (0.238 g, 6.27 mmol) in anhydrous tetrahydrofuran (20 mL) at 0° C. and stirred for 0.5 hour. To this mixture is added dropwise a solution of [4-(2-chloro-3-methylphenyl)piperazine-1-yl]-(3,4,5-trimethoxy-phenyl)methanone (2.12 g, 5.23 mmol) in anhydrous tetrahydrofuran (20 mL). The suspension is stirred for 2 hours at 0° C., followed by dropwise addition of 2N sodium hydroxide. The mixture is filtered through Celite and concentrated in vacuo. The resulting product is purified by MPLC on silica gel eluting with 40% ethyl acetate/hexane to give 1.74 g of the title compound as a white solid; mp 112–113° C.

In a process analogous to Example 1 using appropriate starting materials, the corresponding compounds of Formula I (Examples 2–29) are prepared as follows:

EXAMPLE 2

1-Phenyl-4-(3,4,5-trimethoxybenzyl)piperazine, monohydrochloride; mp 270° C.

EXAMPLE 3

1-(2-Chlorophenyl)-4-(3,4,5-trimethoxybenzyl)-piperazine, monohydrochloride; mp 234–235° C.

EXAMPLE 4

1-(3-Chlorophenyl)-4-(3,4,5-trimethoxybenzyl)-piperazine, monohydrochloride; mp 252° C. (dec).

EXAMPLE 5

1-(4-Chlorophenyl)-4-(3,4,5-trimethoxybenzyl)-piperazine; mp 72–75° C.

EXAMPLE 6

1-o-Tolyl-4-(3,4,5-trimethoxybenzyl)piperazine, monohydrochloride; mp 216–219° C.

EXAMPLE 7

1-m-Tolyl-4-(3,4,5-trimethoxybenzyl)piperazine, monohydrochloride; mp 260° C. (dec).

EXAMPLE 8

1-p-Tolyl-4-(3,4,5-trimethoxybenzyl)piperazine, monohydrochloride; mp 267° C. (dec).

EXAMPLE 9

1-(2-Methoxyphenyl)-4-(3,4,5-trimethoxybenzyl)-piperazine, monohydrochloride; mp 231° C.

EXAMPLE 10

1-(3-Methoxyphenyl)-4-(3,4,5-trimethoxybenzyl)-piperazine, monohydrochloride; mp 242–244° C. (dec).

EXAMPLE 11

1-(4-Methoxyphenyl)-4-(3,4,5-trimethoxybenzyl)-piperazine, monohydrochloride; mp 267° C. (dec).

EXAMPLE 12

1-(2,5-Dichlorophenyl)-4-(3,4,5-trimethoxybenzyl)-piperazine, monohydrochloride; mp 247° C. (dec).

EXAMPLE 13

1-(2,3-Dichlorophenyl)-4-(3,4,5-trimethoxybenzyl)-piperazine, mp 126–129° C.

EXAMPLE 14

1-(3,4-Dichlorophenyl)-4-(3,4,5-trimethoxybenzyl)-piperazine, mp 136–139° C.

EXAMPLE 15

1-(2,3-Dimethylphenyl)-4-(3,4,5-trimethoxybenzyl)-piperazine, monohydrochloride; mp 231–234° C. (dec).

EXAMPLE 16

1-(3,4-Dimethylphenyl)-4-(3,4,5-trimethoxybenzyl)-piperazine, mp 82–84° C.

EXAMPLE 17

1-(2-Chloro-4-methylphenyl)-4-(3,4,5-trimethoxybenzyl)-piperazine, monohydrochloride; mp 216–218° C.

13

EXAMPLE 18

1-(2-Chloro-5-methylphenyl)-4-(3,4,5-trimethoxybenzyl)-piperazine, monohydrochloride; mp 230° C.

EXAMPLE 19

1-(3-Chloro-2-methylphenyl)-4-(3,4,5-trimethoxybenzyl)-piperazine, monohydrochloride; mp 225–227° C.

EXAMPLE 20

1-(3-Chloro-4-methylphenyl)-4-(3,4,5-trimethoxybenzyl)-piperazine, monohydrochloride; mp 220° C.

EXAMPLE 21

1-(5-Chloro-2-methylphenyl)-4-(3,4,5-trimethoxybenzyl)-piperazine, monohydrochloride; mp 199–202° C.

EXAMPLE 22

1-(4-Chloro-2-methylphenyl)-4-(3,4,5-trimethoxybenzyl)-piperazine, monohydrochloride; mp 175–178° C.

EXAMPLE 23

1-(4-Chloro-3-methylphenyl)-4-(3,4,5-trimethoxybenzyl)-piperazine, monohydrochloride; mp 251–253° C.

EXAMPLE 24

1-Pyridin-2-yl-4-(3,4,5-trimethoxybenzyl)piperazine, monohydrochloride; mp 262–265° C.

EXAMPLE 25

4-Phenyl-1-(3,4,5-trimethoxybenzyl)piperidine, monohydrochloride; mp 230° C.

EXAMPLE 26

1-(2-Chloro-3-methylphenyl)-4-(2,3-dimethoxybenzyl)-piperazine, monohydrochloride; mp 183–185° C.

EXAMPLE 27

1-(2-Chloro-3-methylphenyl)-4-(2,4-dimethoxybenzyl)-piperazine, monohydrochloride; mp 103–106° C.

EXAMPLE 28

1-(2-Chloro-3-methylphenyl)-4-(2,5-dimethoxybenzyl)-piperazine, monohydrochloride; mp 115–119° C.

EXAMPLE 29

1-(2-Chloro-3-methylphenyl)-4-(3,4-dimethoxybenzyl)-piperazine, monohydrochloride; mp 193–196° C.

14

We claim:
1. A compound of Formula I

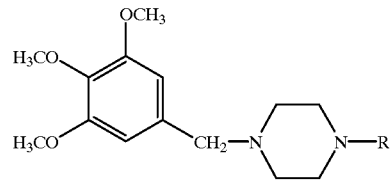

whereas R is
4-,5-,6-, or 7-benzo[b]furanyl,
4-,5-,6-, or 7-benzo[b]thienyl,
4-,5-,6-, or 7-indolyl,
2-,3-,4-,5-,6-,7-, or 8-quinolinyl, or
2-,3-,4-,5-,6-,7-, or 8-isoquionlinyl;
or a pharmaceutically acceptable acid addition salt thereof.

2. A pharmaceutical composition comprising a compound according to claim 1 in admixture with a pharmaceutically acceptable excipient, diluent, or carrier.

3. A method of treating psychoses comprising administering to a host suffering therefrom a therapeutically effective amount of a compound of Formula I

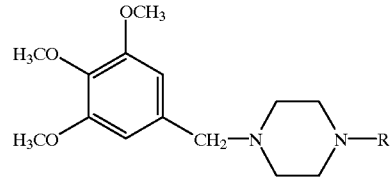

wherein R is a phenyl group or phenyl group substituted by 1 to 4 substituents selected from the group consisting of lower alkyl, lower alkoxy, lower thioalkoxy, halogen, nitro, amino, and cyano,
2-, 3- or 4-pyridinyl,
4-, 5-, 6-, or 7-benzo[b]furanyl,
4-, 5-, 6-, or 7-benzo[b]thienyl,
4-, 5-, 6-, or 7-indolyl,
2-, 3-, 4-, 5-, 6-, 7-, or 8-isoquinolinyl; or a pharmaceutically acceptable acid addition salt thereof.

4. The method of claim 3 wherein a compound of Formula I is selected from the group consisting of:
1-phenyl-4-(3,4,5-trimethoxybenzyl)-piperazine;
1-(2-chlorophenyl)-4-(3,4,5-trimethoxybenzyl)-piperazine;
1-(3-chlorophenyl)-4-(3,4,5-trimethoxybenzyl) piperazine;
1-(4-chlorophenyl)-4-(3,4,5-trimethoxybenzyl) piperazine;
1-o-tolyl-4-(3,4,5-trimethoxybenzyl)piperazine;
1-m-tolyl-4-(3,4,5-trimethoxybenzyl)piperazine;
1-p-tolyl-4-(3,4,5-trimethoxybenzyl)piperazine;
1-(2-methoxyphenyl)-4-(3,4,5-trimethoxybenzyl)-piperazine;
1-(3-methoxyphenyl)-4-(3,4,5-trimethoxybenzyl)-piperazine;
1-(4-methoxyphenyl)-4-(3,4,5-trimethoxybenzyl)-piperazine;

1-(2,5-dichlorophenyl)-4-(3,4,5-trimethoxybenzyl)-piperazine;
1-(2,3-dichlorophenyl)-4-(3,4,5-trimethoxybenzyl)-piperazine;
1-(3,4-dichlorophenyl)-4-(3,4,5-trimethoxybenzyl)-piperazine;
1-(2,3-dimethylphenyl)-4-(3,4,5-trimethoxybenzyl)-piperazine;
1-(3,4-dimethylphenyl)-4-(3,4,5-trimethoxybenzyl)-piperazine;
1-(2-chloro-3-methylphenyl)-4-(3,4,5-trimethoxybenzyl)piperazine;
1-(2-chloro-4-methylphenyl)-4-(3,4,5-trimethoxybenzyl)piperazine;
1-(2-chloro-5-methylphenyl)-4-(3,4,5-trimethoxybenzyl)piperazine;
1-(3-chloro-2-methylphenyl)-4-(3,4,5-trimethoxybenzyl)piperazine;
1-(3-chloro-4-methylphenyl)-4-(3,4,5-trimethoxybenzyl)piperazine;
1-(5-chloro-2-methylphenyl)-4-(3,4,5-trimethoxybenzyl)piperazine;
1-(4-chloro-2-methylphenyl)-4-(3,4,5-trimethoxybenzyl)piperazine;
1-(4-chloro-3-methylphenyl)-4-(3,4,5-trimethoxybenzyl)piperazine; and
1-pyridin-2-yl-4-(3,4,5-trimethoxybenzyl)-piperazine.

5. The method of claim 3 wherein the psychosis is schizophrenia.

6. The method of claim 4 wherein the psychosis is schizophrenia.

* * * * *